(12) United States Patent
Yoshida et al.

(10) Patent No.: US 11,800,259 B2
(45) Date of Patent: *Oct. 24, 2023

(54) BIOLOGICAL MONITORING DEVICE

(71) Applicants: SEIKO GROUP CORPORATION, Tokyo (JP); Science Energy CO., Ltd., Tokyo (JP)

(72) Inventors: Yoshifumi Yoshida, Tokyo (JP); Ryosuke Isogai, Tokyo (JP); Kotaro Maki, Tokyo (JP)

(73) Assignees: Seiko Group Corporation, Tokyo (JP); Seiko Science Energy Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/474,635

(22) Filed: Sep. 14, 2021

(65) Prior Publication Data
US 2022/0103915 A1 Mar. 31, 2022

(30) Foreign Application Priority Data
Sep. 30, 2020 (JP) .................. 2020-165898

(51) Int. Cl.
*H04Q 9/00* (2006.01)
*A61B 5/00* (2006.01)

(52) U.S. Cl.
CPC .............. *H04Q 9/00* (2013.01); *A61B 5/682* (2013.01); *H04Q 2209/82* (2013.01)

(58) Field of Classification Search
CPC .. H04Q 9/00; H04Q 2209/00; H04Q 2209/40; H04Q 2209/43; H04Q 2209/80;
(Continued)

(56) References Cited

U.S. PATENT DOCUMENTS 7,257,438 B2 * 8/2007 Kinast .................. A61B 5/6822
600/509
10,067,531 B2 * 9/2018 Maufort ................ G06F 21/445
(Continued)

FOREIGN PATENT DOCUMENTS

CN 107518952 A 12/2017
EP 3199125 A1 8/2017
(Continued)

OTHER PUBLICATIONS

Extended European Search Report in Europe Application No. 21196496.0, dated Feb. 21, 2022, 9 pages.
(Continued)

*Primary Examiner* — Franklin D Balseca
(74) *Attorney, Agent, or Firm* — Crowell & Moring LLP

(57) ABSTRACT

A biological monitoring device includes a sensor included in a sensor device, performing a detection process of detecting a medical condition of a patient, and performing a process of generating first detection data indicating a result of the detection process, a generation unit realized by the sensor device, indicating contents related to the detection process, and performing a process of generating second detection data having a smaller data volume than the first detection data, on the basis of the first detection data, and a communication unit realized by the sensor device, and performing a process of transmitting the second detection data to a terminal associated with the patient.

11 Claims, 5 Drawing Sheets

(58) Field of Classification Search
CPC .......... H04Q 2209/82; H04Q 2209/826; A61B 5/0002; A61B 5/0004; A61B 5/0006; A61B 5/0008; A61B 5/0015; A61B 5/68; A61B 5/6801; A61B 5/6802; A61B 5/6813; A61B 5/682
See application file for complete search history.

(56) References Cited

U.S. PATENT DOCUMENTS

| | | |
|---|---|---|
| 2010/0152599 A1 | 6/2010 | DuHamel et al. |
| 2017/0347956 A1 | 12/2017 | Zegarelli |
| 2019/0320977 A1 | 10/2019 | Anderson et al. |
| 2020/0409409 A1* | 12/2020 | Xie ..................... H04W 4/025 |
| 2022/0095918 A1* | 3/2022 | Yoshida ............... A61B 5/0004 |

FOREIGN PATENT DOCUMENTS

| | | | |
|---|---|---|---|
| JP | 4264472 B | 5/2009 | |
| JP | 2015-188558 A | 11/2015 | |
| JP | 6376588 B | 8/2018 | |
| WO | WO 2019/005808 A1 | 1/2019 | |
| WO | WO-2019005808 A1 * | 1/2019 | ........... A61B 5/1111 |

OTHER PUBLICATIONS

Extended European Search Report regarding 21196500.9 dated Feb. 21, 2022.

* cited by examiner

BIOLOGICAL MONITORING DEVICE

RELATED APPLICATIONS

This application claims priority to Japanese Patent Application No. 2020-165898, filed on Sep. 30, 2020, the entire content of which is incorporated herein by reference.

BACKGROUND OF THE INVENTION

1. Field of the Invention

The present invention relates to a biological monitoring device.

2. Description of the Related Art

Currently, a technique has progressively been developed so that a medical condition of a patient is detected by a sensor attached to a medical device or medical instrument used in a body of the patient and medical treatment is performed on the patient, based on a detected result.

For example, Japanese Patent No. 4264472 discloses an intraoral-installing type biological monitor/treatment device including a biological sensor, a signal processing unit, a communication unit, and an operating equipment unit.

The biological sensor is incorporated in a denture base or a mouthpiece. The biological sensor is a sensor that detects a pulse, a blood oxygen level, an enzyme or a metabolite in saliva, or an acceleration sensor that detects a body posture or a motion. The signal processing unit evaluates data obtained from the biological sensor, detects an abnormal value, and stores the data. The communication unit wirelessly transmits the data in the signal processing unit to a network such as a home network or the Internet via a network connector, and receives a command signal from a management center. The operating equipment unit is a drug pump operated based on the command signal transmitted from the management center via the network, a calling vibrator, or an intraoral telephone device.

However, the above-described intraoral-installing type biological monitor/treatment device receives the command signal from the management center, and wirelessly transmits the data from the biological sensor to the network to operate the operating equipment unit. However, the intraoral-installing type biological monitor/treatment device does not transmit the data from the biological sensor to a patient. In addition, the data from the biological sensor does not always indicate contents which can be easily understood by the patient.

Therefore, the above-described intraoral-installing type biological monitor/treatment device cannot notify the patient of information related to treatment of the patient himself or herself. Therefore, even when the intraoral-installing type biological monitor/treatment device is used, it may not be possible to increase a motivation of the patient for the treatment in some cases.

SUMMARY OF THE INVENTION

The present invention aims to provide a biological monitoring device capable of increasing a motivation of a patient for a detection process of detecting a medical condition of the patient.

(1) According to one aspect of the present invention, there is provided a biological monitoring device including a sensor included in a sensor device, performing a detection process of detecting a medical condition of a patient, and performing a process of generating first detection data indicating a result of the detection process, a generation unit realized by the sensor device, and performing a process of generating second detection data indicating contents related to the detection process and having a smaller data volume than the first detection data, on the basis of the first detection data, and a communication unit realized by the sensor device, and performing a process of transmitting the second detection data to a terminal associated with the patient.

(2) The communication unit may transmit the second detection data to the terminal without receiving a request for transmitting the second detection data to the terminal.

(3) The biological monitoring device may further include a determination unit realized by the sensor device, and determining whether or not the sensor device exists in a body of the patient, on the basis of at least one of the first detection data and the second detection data, and a control unit realized by the sensor device, and controlling the communication unit to transmit the second detection data to the terminal in a first cycle, when it is determined that the sensor device exists in the body of the patient.

(4) When it is determined that the sensor device does not exist in the body of the patient, the control unit may control the communication unit to transmit the second detection data to the terminal in a second cycle shorter than the first cycle.

(5) The determination unit may calculate a time during which the sensor device does not exist in the body of the patient, on the basis of at least one of the first detection data and the second detection data, and is further configured to determine whether or not the time exceeds a predetermined threshold. The control unit may lengthen the second cycle when it is determined that the time exceeds the predetermined threshold.

(6) The biological monitoring device may further include a determination unit calculating a time during which the sensor device does not exist in a body of the patient, on the basis of at least one of the first detection data and the second detection data, and determining whether or not the time exceeds a predetermined threshold. When it is determined that the time exceeds the predetermined threshold, the generation unit may generate recommendation data for causing the terminal to perform a process of outputting information recommending the patient to be in a state where the sensor device exists in the body of the patient. The communication unit may transmit the recommendation data to the terminal.

(7) The biological monitoring device may further include a storage unit that is configured to store the first detection data.

According to the present invention, it is possible to increase a motivation of a patient for a detection process of detecting a medical condition of the patient.

DETAILED DESCRIPTION OF THE PREFERRED EMBODIMENTS

Embodiment

An example of a biological monitoring device, a terminal, and a data acquisition device according to an embodiment will be described with reference to FIGS. 1 to 5.

Figure 1:
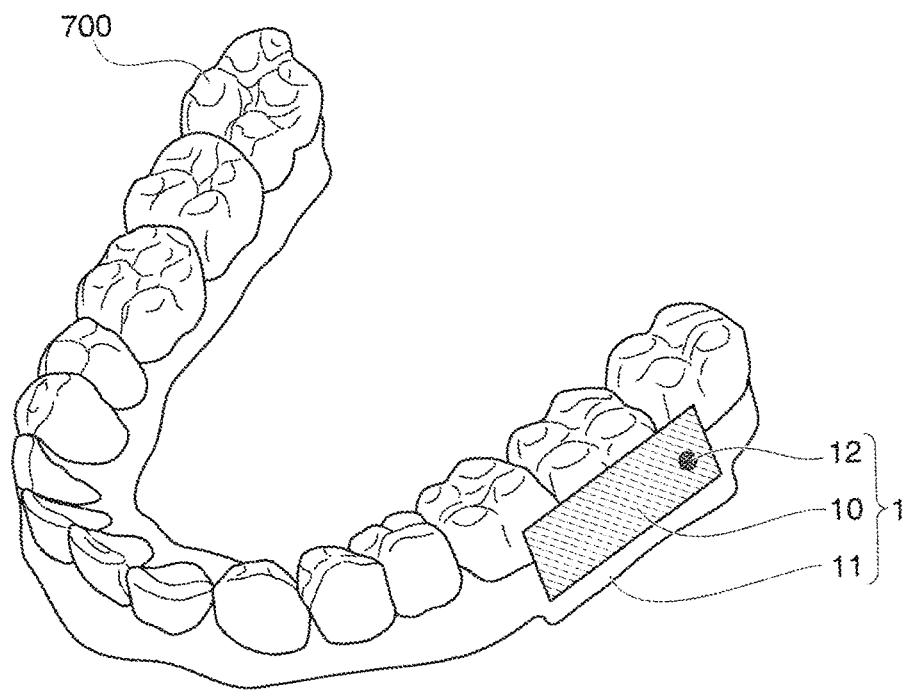
FIG. 1 is a view showing an example of an appearance of a biological monitoring device according to an embodiment.
Figure 2:
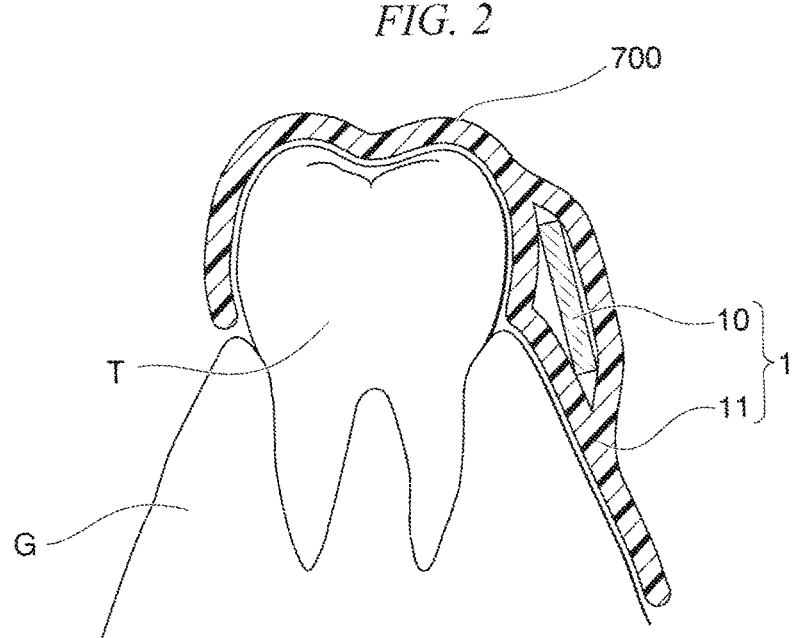
FIG. 2 is a view showing an example of a cross section of a sensor device and a fixing unit which are included in the biological monitoring device according to the embodiment.
Figure 3:
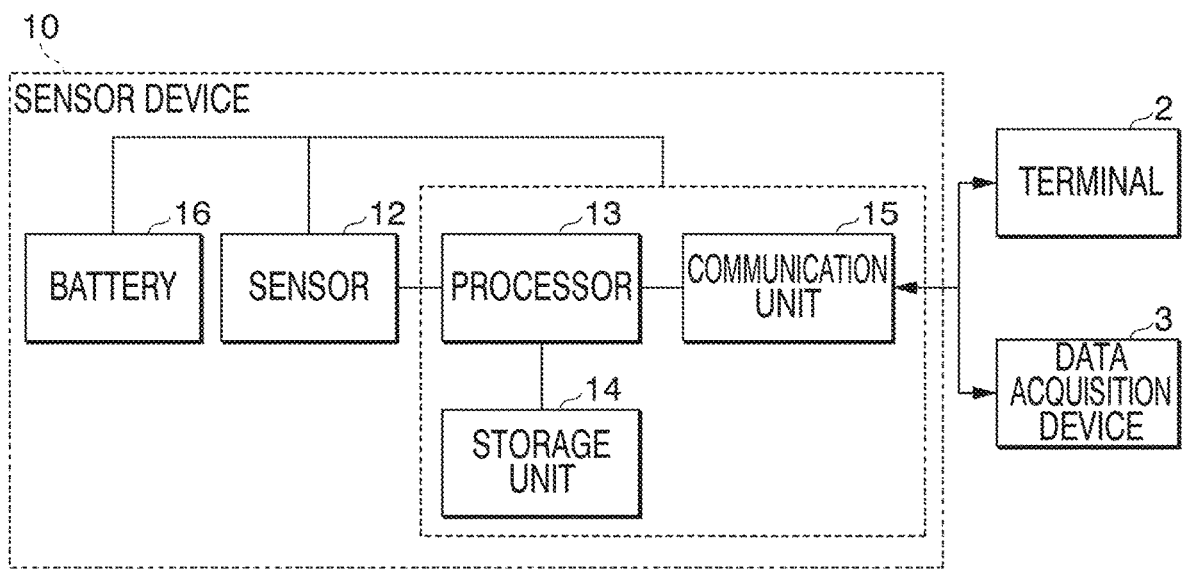
FIG. 3 is a view showing an example of the sensor device, a terminal, and a data acquisition device according to the embodiment.

FIG. 1 is a view showing an example of an appearance of the biological monitoring device according to the embodiment. FIG. 2 is a view showing an example of a cross section of a sensor device and a fixing unit which are included in the biological monitoring device according to the embodiment. FIG. 3 is a view showing an example of the sensor device, the terminal, and the data acquisition device according to the embodiment.

As shown in FIGS. 1 and 2, a biological monitoring device 1 includes a sensor device 10 and a fixing unit 11. As shown in FIG. 3, the sensor device 10 includes a sensor 12, a processor 13, a storage unit 14, a communication unit 15, and a battery 16.

The fixing unit 11 is a member that fixes the sensor device 10 in a body of a patient. For example, an interior of the body of the patient referred to herein is an interior of an oral cavity, a nasal cavity, or an ear canal of the patient. However, the interior of the body of the patient referred to herein may include sites other than the oral cavity, the nasal cavity, and the ear canal of the patient.

For example, as shown in FIGS. 1 and 2, the fixing unit 11 is partially connected to an orthodontic appliance 700, and is a resin-made member for fixing the sensor device 10 to an outer side of a mandibular body of a mandible bone of the patient. As shown in FIG. 2, it is preferable that the fixing unit 11 seals the sensor device 10 to avoid water such as saliva of the patient from adhering to the sensor device 10.

The sensor 12 is included in the sensor device 10, performs a detection process of detecting a medical condition of the patient, and performs a process of generating first detection data indicating a result of the detection process. For example, the first detection data is data indicating a physical quantity detected by the detection process, and may indicate whether or not the detection process is normally performed. The sensor 12 may be controlled by an integrated circuit (IC), and may intermittently be operated every 10 seconds, for example.

For example, the sensor 12 is a pulse oximeter. The pulse oximeter includes a light emitting element such as a light emitting diode (LED) and a photo detection element. The pulse oximeter applies light output from the light emitting element to an inner side of a cheek of the patient, and causes the photo detection element to detect the light reflected on the cheek of the patient. The pulse oximeter measures a blood oxygen level, based on the light detected by the photo detection element, and generates first detection data indicating the blood oxygen level of the patient.

However, for example, the sensor 12 may be a chemical sensor, an acceleration sensor, a gyro sensor, a pressure sensor, a strain sensor, a pulse wave sensor, a heart rate sensor, or a blood flow sensor.

The chemical sensor is a sensor that generates the first detection data indicating a type or the number of bacteria existing in the body of the patient by detecting the presence or absence of a specific chemical substance existing in the body of the patient, or by measuring a concentration of the specific chemical substance existing in the body of the patient.

The acceleration sensor is a sensor that performs a detection process of measuring acceleration of a part of the body of the patient, and generates the first detection data indicating the number of walking steps, the amount of activity, and a movement of the part of the body, for example. The gyro sensor is a sensor that performs a detection process of measuring an angular velocity of a part of the body of the patient, and measures the number of walking steps, the amount of activity, and a movement of the part of the body, for example. For example, the part of the body of the patient referred to herein is a jaw of the patient.

When the biological monitoring device 1 is attached to the jaw of the patient, and the sensor 12 includes at least one of the acceleration sensor and the gyro sensor, for example, the sensor 12 generates the first detection data indicating the number of chewing times of the patient, the number of swallowing times of the patient, and the number of teeth grinding times.

The pressure sensor is a sensor that performs a detection process of measuring a pressure applied to a part of the body of the patient, and generates the first detection data indicating a movement of the part of the body of the patient. The strain sensor is a sensor that performs a detection process of measuring a strain applied to a part of the body of the patient, and generates the first detection data indicating a movement of the part of the body of the patient. For example, the part of the body of the patient referred to herein is a jaw of the patient.

When the biological monitoring device 1 is attached to the jaw of the patient, and the sensor 12 includes at least one of the pressure sensor and the strain sensor, for example, the sensor 12 can measure a magnitude of a force applied to teeth, artificial teeth, and an orthodontic appliance by the number of chewing times and chewing. In this case, for example, the sensor 12 can measure a magnitude of a force applied to teeth, artificial teeth, and an orthodontic appliance by the number of swallowing times, the number of teeth grinding times, and teeth grinding, or a time during which the orthodontic appliance is mounted.

The pulse wave sensor is a sensor that measures a pulse wave by using the light, and generates the first detection data indicating the pulse wave of the patient. The heart rate sensor is a sensor that measures a heart rate of the patient by using the light, and generates the first detection data indicating the heart rate of the patient. The blood flow sensor is a sensor that measures a blood flow of the patient by using a laser, and generates the first detection data indicating the blood flow of the patient.

When a sensor using the light such as the laser is included in the sensor 12, at least a portion of the fixing unit 11 needs to be made of a material that transmits the light. For example, when a sensor using the light having a wavelength belonging to a near infrared region or a visible light region is included in the sensor 12, at least a portion of the fixing unit 11 needs to be made of a material that transmits the light having a wavelength of 400 nm to 1,000 nm.

For example, the processor 13 is a central processing unit (CPU). The processor 13 reads and executes a program stored in the storage unit 14, and realizes a function of controlling the sensor 12, a function of controlling the communication unit 15, and other functions. The processor 13 reads and executes a program stored in the storage unit 14, and realizes a generation unit 131, a determination unit 132, and a control unit 133 which will be described later.

For example, the storage unit 14 includes a read only memory (ROM) and a random access memory (RAM). For example, the ROM included in the storage unit 14 stores the program read and executed by the processor 13. On the other hand, in the RAM included in the storage unit 14, the program read and executed by the processor 13 is developed. Furthermore, the storage unit 14 stores the first detection data generated by the sensor 12.

The communication unit 15 communicates with the terminal 2, the data acquisition device 3, and other devices which are shown in FIG. 3. For example, the communication unit 15 communicates with the terminal 2, the data acquisition device 3, and other devices by using wireless communication such as Bluetooth (registered trademark) Low Energy (BLE). In this case, the communication unit 15 has a circuit corresponding to a BLE standard.

The terminal 2 is a terminal such as a smartphone or a tablet associated with the patient on which the biological monitoring device 1 is mounted. For example, the terminal includes a terminal associated with the patient himself or herself on which the biological monitoring device 1 is mounted, a guardian of the patient, or an attending physician of the patient. The terminal 2 may perform a scan response to the biological monitoring device 1 when necessary, and may request the biological monitoring device 1 to additionally transmit second detection data.

The data acquisition device 3 acquires the first detection data generated by the biological monitoring device 1, and transmits the first detection data to a computer used by the attending physician, a dental hygienist, or a nurse of the patient. For example, the first detection data is used in the computer for examining an advantageous effect of treatment performed on the patient, examining a future treatment policy, and analyzing a medical condition of the patient.

The battery 16 supplies power to each unit of the sensor device 10, for example, the sensor 12, the processor 13, the storage unit 14, and the communication unit 15.

Figure 4:
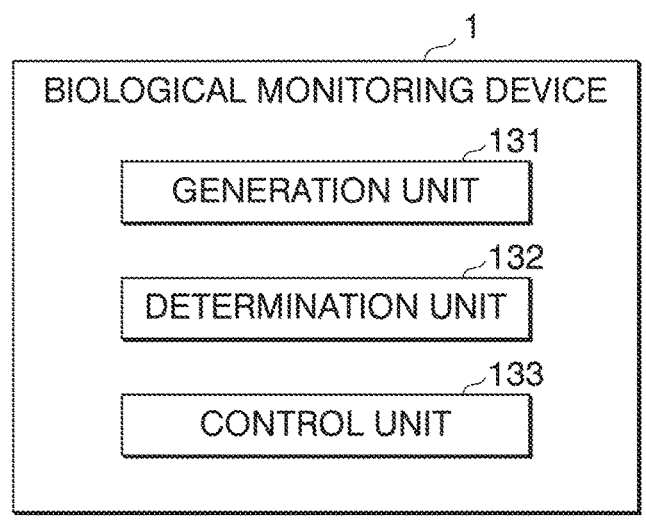
FIG. 4 is a view showing an example of a functional configuration of the biological monitoring device according to the embodiment.

FIG. 4 is a view showing an example of a functional configuration of the biological monitoring device according to the embodiment.

As shown in FIG. 4, the biological monitoring device 1 includes the generation unit 131, the determination unit 132, and the control unit 133. The generation unit 131, the determination unit 132, and the control unit 133 are realized in such a manner that the processor 13 reads and executes a program stored in the storage unit 14.

The generation unit 131 indicates contents related to a detection process performed by the sensor 12, and performs a process of generating the second detection data having a smaller data volume than the first detection data, based on the first detection data. The generation unit 131 may continuously perform the process of generating the second detection data, as long as the sensor 12 continuously perform the detection process.

For example, the second detection data indicates a portion of the contents indicated by the first detection data, a value calculated based on the first detection data, and the amount of power that can be supplied to the sensor 12 by the battery 16. Unlike the first detection data, the second detection data is not data used by the attending physician, the dental hygienist, or the nurse of the patient for the treatment of the patient or a medical research, and is a history of using the orthodontic appliance 700 or data used to easily notify the patient of a past health condition of the patient. Therefore, it is preferable that the second detection data indicates the contents that are easy for the patient to understand rather than medically accurate contents.

The second detection data is transmitted to the terminal 2 by the communication unit 15. In this case, the communication unit 15 may transmit the second data to the terminal 2 without receiving a request for transmitting the second detection data to the terminal 2. For example, the communication unit 15 may transmit the second detection data to the terminal 2 by using an advertising packet, a beacon, or a broadcast.

Figure 5:
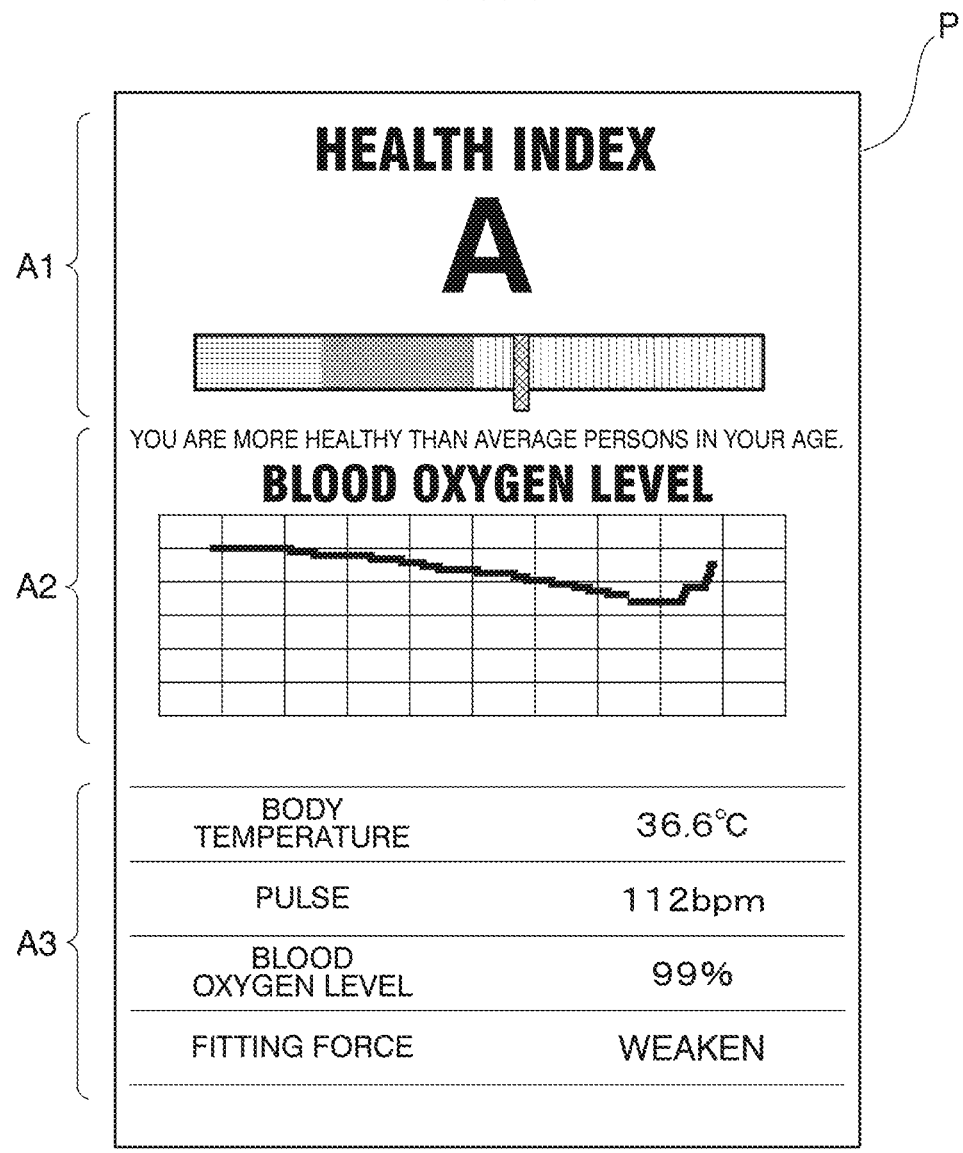
FIG. 5 is a view showing an example of an image displayed on a display mounted on the terminal, based on second detection data generated by the sensor device according to the embodiment.

FIG. 5 is a view showing an example of an image displayed on a display mounted on the terminal, based on the second detection data generated by the sensor device 10 according to the embodiment. An image P shown in FIG. 5 includes a display region A1, a display region A2, and a display region A3.

A region having horizontal line hatching displayed in the display region A1 indicates a range in which a health index is relatively low. A region having dot hatching displayed in the display region A1 indicates a range in which the health index is approximately medium. A region having vertical line hatching displayed in the display region A1 indicates a range in which the health index is relatively high.

A region having oblique hatching displayed in the display region A1 is a cursor indicating a current health index of the patient. For example, as shown in FIG. 5, when the cursor indicates a health index in the region having the vertical line hatching, it is displayed in the display region A1 that the health index is "A". Alternatively, when the cursor indicates a health index in the region having the dot hatching, it is displayed in the display region A1 that the health index is "B". Alternatively, when the cursor indicates a health index in the region having the horizontal line hatching, it is displayed in the display region A1 that the health index is "C".

The display region A2 displays a graph of a blood oxygen level measured by the sensor 12. In the graph, a horizontal axis represents a time, and a vertical axis represents the blood oxygen level. The graph shown in FIG. 5 shows an example of a measurement result when the blood oxygen level increases toward a normal blood oxygen level after the blood oxygen level gradually and continuously decreases.

The display region A3 indicates that a current body temperature of the patient is "36.6° C.", a pulse is "112 bpm", and the blood oxygen level is "99%", and indicates that a fitting force of the patient is weak.

The determination unit 132 determines whether or not the sensor device 10 exists in the body of the patient, based on at least one of the first detection data and the second detection data. For example, the determination unit 132 determines that the sensor device 10 exists in the body of the patient, when at least one of the blood oxygen level indicated by the first detection data and the blood oxygen level indicated by the second detection data is relatively close to the blood oxygen level of a healthy person. On the other hand, the determination unit 132 determines the sensor device 10 does not exist in the body of the patient, when at least one of the blood oxygen level indicated by the first detection data and the blood oxygen level indicated by the second detection data is not a significant blood oxygen level.

When it is determined that the sensor device 10 exists in the body of the patient, the control unit 133 controls the communication unit 15 to transmit the second detection data to the terminal 2 in a first cycle. The first cycle is a cycle that can be set to any desired length, and is five minutes, for example. On the other hand, when it is determined that the sensor device 10 does not exist in the body of the patient, the control unit 133 controls the communication unit 15 to transmit the second detection data to the terminal 2 in a second cycle shorter than the first cycle. The second cycle is a cycle that can be set to any desired length, and is 5 seconds, for example.

A wireless signal transmitted to the terminal 2 by the communication unit 15 is greatly attenuated by receiving influence of water existing in the body or a tissue of the patient. Therefore, the communication unit 15 needs to increase intensity of the wireless signal to transmit the second detection data to an outside of the body when the sensor device 10 exists in the body of the patient than when the sensor device 10 exists outside the body of the patient. Therefore, the communication unit 15 consumes more power when the sensor device 10 exists in the body of the patient.

The determination unit 132 may calculate a time during which the sensor device 10 does not exist in the body of the patient, based on at least one of the first detection data and the second detection data, and may further determine whether or not the time exceeds a predetermined threshold. When it is determined that the time exceeds the predetermined threshold, the control unit 133 may lengthen the second cycle. In this case, the control unit 133 may lengthen the second cycle within a range not exceeding a length of the first cycle, or may lengthen the second cycle regardless of the length of the first cycle.

The determination unit 132 may calculate a time during which the sensor device 10 does not exist in the body of the patient, based on at least one of the first detection data and the second detection data, and may further determine whether or not the time exceeds a predetermined threshold. When it is determined that the time exceeds the predetermined threshold, the generation unit 131 generates recommendation data for causing the terminal 2 to perform a process of outputting information for recommending the patient to be in a state where the sensor device 10 exists in the body of the patient. The recommendation data is transmitted to the terminal 2 by the communication unit 15, and is used by the terminal 2 to output the information by using a display or a speaker mounted on the terminal 2.

Next, an example of a process of determining a cycle in which the biological monitoring device according to the embodiment transmits the second detection data to the terminal will be described with reference to FIG. 6.

Figure 6:
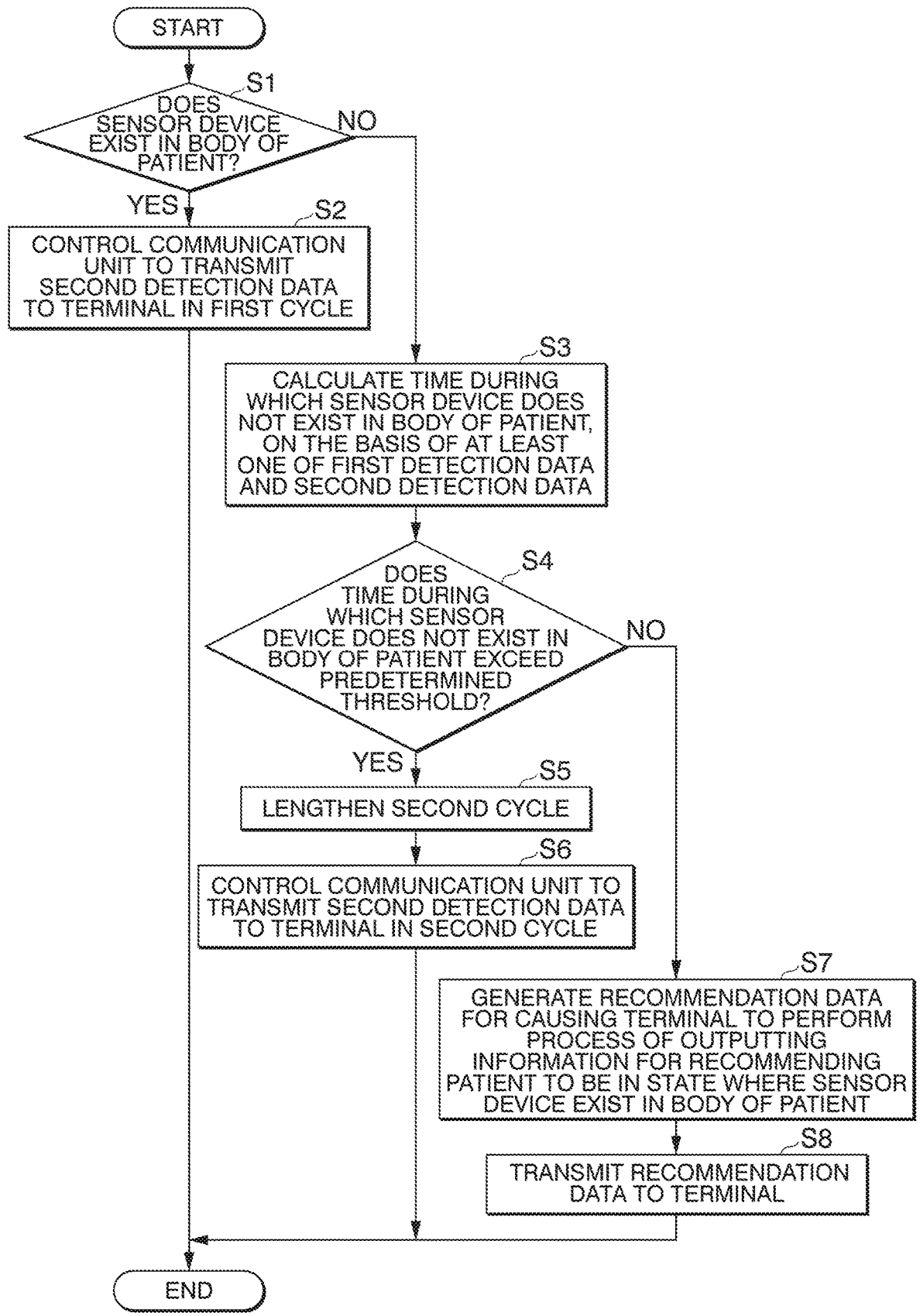
FIG. 6 is a flowchart showing an example of a process of determining a cycle in which the biological monitoring device according to the embodiment transmits the second detection data to the terminal.

FIG. 6 is a flowchart showing an example of the process of determining the cycle in which the biological monitoring device according to the embodiment transmits the second detection data to the terminal. The process shown in FIG. 6 is a process performed on a premise that the sensor 12 and the generation unit 131 are continuously operated.

In Step S1, the determination unit 132 determines whether or not the sensor device 10 exists in the body of the patient. When the determination unit 132 determines that the sensor device 10 exists in the body of the patient (Step S1: YES), the process proceeds to Step S2. On the other hand, when the determination unit 132 determines that the sensor device 10 does not exist in the body of the patient (Step S1: NO), the process proceeds to Step S3.

In Step S2, the control unit 133 controls the communication unit 15 to transmit the second detection data to the terminal 2 in the first cycle.

In Step S3, the determination unit 132 calculates a time during which the sensor device 10 does not exist in the body of the patient, based on at least one of the first detection data and the second detection data.

In Step S4, the determination unit 132 determines whether or not the time during which the sensor device 10 does not exist in the body of the patient exceeds a predetermined threshold. When the determination unit 132 determines that the time during which the sensor device 10 does not exist in the body of the patient exceeds the predetermined threshold (Step S3: YES), the process proceeds to Step S5. On the other hand, when the determination unit 132 determines that the time during which the sensor device 10 does not exist in the body of the patient is equal to or smaller than the predetermined threshold (Step S3: NO), the process proceeds to Step S7.

In Step S5, the control unit 133 lengthens the second cycle.

In Step S6, the control unit 133 controls the communication unit 15 to transmit the second detection data to the terminal 2 in the second cycle.

In Step S7, the generation unit 131 generates recommendation data for causing the terminal 2 to perform a process of outputting information recommending the patient to be in a state where the sensor device 10 exists in the body of the patient.

In Step S8, the communication unit 15 transmits the recommendation data to the terminal 2.

Hitherto, the biological monitoring device 1 according to the embodiment has been described.

The biological monitoring device 1 includes the sensor 12, the generation unit 131, and the communication unit 15. The sensor 12 is included in the sensor device 10, performs a detection process of detecting a medical condition of the patient, and performs a process of generating first detection data indicating a result of the detection process. The generation unit 131 is realized by the sensor device 10, indicates the contents related to the detection process, and performs the process of generating the second detection data having a smaller data volume than the first detection data, based on the first detection data. The communication unit 15 is realized by the sensor device 10, and performs the process of transmitting the second detection data to the terminal 2 associated with the patient.

In this manner, the biological monitoring device 1 can transmit the second detection data to the terminal 2 associated with the patient, can easily notify the patient of the contents of the detection process, and can increase a motivation of the patient for a detection process of detecting a medical condition of the patient.

The biological monitoring device 1 can notify the patient of information related to a health condition of the patient himself or herself, when the second detection data indicates the blood oxygen level of the patient, the number of walking steps, the amount of activity, and a type or the number of bacteria existing in the body. Furthermore, the biological monitoring device 1 can notify the patient of information related to a tooth condition of the patient himself or herself, when the second detection data indicates the number of chewing times of the patient, a magnitude of a force applied to teeth, artificial teeth, and an orthodontic appliance by the number of chewing times of the patient and chewing, or a magnitude of a force applied to the teeth, the artificial teeth, and the orthodontic appliance by the number of teeth grinding times and teeth grinding.

The biological monitoring device 1 transmits the second detection data to the terminal 2 without receiving a request for transmitting the second detection data to the terminal 2.

In this manner, the biological monitoring device 1 does not communicate with the terminal 2 before transmitting the second detection data to the terminal 2. Accordingly, the biological monitoring device 1 can save the power supplied from the battery 16, and can continuously extend the operable time.

When it is determined that the sensor device 10 exists in the body of the patient, the biological monitoring device 1 controls the communication unit 15 to transmit the second detection data to the terminal 2 in the first cycle. On the other hand, when it is determined that the sensor device 10 does not exist in the body of the patient, the biological monitoring device 1 controls the communication unit 15 to transmit the second detection data to the terminal 2 in the second cycle shorter than the first cycle.

That is, when the biological monitoring device 1 needs to consume a large amount of the power to transmit the second detection data to the terminal 2 since the sensor device 10 exists in the body of the patient, the biological monitoring device 1 adopts the first cycle longer than the second cycle, as a cycle for transmitting the second detection data.

In this manner, when the biological monitoring device 1 needs to consume a large amount of the power to transmit the second detection data to the terminal 2, the biological monitoring device 1 adopts the first cycle longer than the second cycle. Accordingly, the biological monitoring device 1 can save the power supplied from the battery 16, and can continuously extend the operable time.

The biological monitoring device 1 calculates a time during which the sensor device 10 does not exist in the body of the patient, based on at least one of the first detection data and the second detection data, and determines whether or not the time exceeds the predetermined threshold. When it is determined that the time exceeds the predetermined threshold, the biological monitoring device 1 lengthens the second cycle.

In this manner, the biological monitoring device 1 does not need to transmit the second detection data to the terminal 2 since the sensor device 10 does not exist in the body of the patient, the biological monitoring device 1 can lengthen the second cycle, can save the power supplied from the battery 16, and can continuously extend the operable time.

The biological monitoring device 1 calculates a time during which the sensor device 10 does not exist in the body of the patient, based on at least one of the first detection data and the second detection data, and determines whether or not the time exceeds the predetermined threshold. Next, when it is determined that the time exceeds the predetermined threshold, the biological monitoring device 1 generates the recommendation data for causing the terminal to perform the process of outputting the information for recommending the patient to be in a state where the sensor device 10 exists in the body of the patient. The biological monitoring device 1 transmits the recommendation data to the terminal 2.

In this manner, when the sensor device 10 does not exist in the body of the patient, the biological monitoring device 1 can urge the patient to mount the biological monitoring device 1, and can more reliably achieve an advantageous effect of treatment using the biological monitoring device 1. In this manner, when the sensor device 10 does not exist in the body of the patient, the biological monitoring device 1 urges the patient to mount the biological monitoring device 1, and can more reliably recognize the health condition obtained by using the biological monitoring device 1.

The biological monitoring device 1 includes the storage unit 14 that stores the first detection data. In this manner, the biological monitoring device 1 may only store the first detection data in the storage unit 14 as long as the biological monitoring device 1 doers not receive a request for transmitting the first detection data from the data acquisition device 3. Therefore, the biological monitoring device 1 does not need to consume the power stored in the battery 16 to transmit the first detection data, and can continuously extend the operable time.

At least some of the functions of the biological monitoring device 1 may be realized by hardware including circuit units (circuitry) such as Large Scale Integration (LSI), Application Specific Integrated Circuit (ASIC), and Field-Programmable Gate Array (FPGA).

The sensor device 10 described above does not need to be fixed to the orthodontic appliance 700 by the fixing unit 11. For example, the sensor device 10 may be fixed to a sprint used by the patient. Even in this case, the biological monitoring device can fix the sensor device 10 in the body of the patient without invading the body of the patient.

In the above-described embodiment, a case where the biological monitoring device 1 is one device has been described as an example. However, the present invention is not limited thereto. For example, a part of the biological monitoring device 1 may be realized by a first device, and another part of the biological monitoring device 1 may be realized by a second device different from the first device. However, it is preferable that all of the devices are sealed by the fixing unit 11.

In the above-described embodiment, a case where the sensor device 10 is sealed by the fixing unit 11 has been described as an example. However, the present invention is not limited thereto. For example, the fixing unit 11 may only cover a portion of the sensor device 10.

In the above-described embodiment, a case where the sensor device 10 includes the CPU, the ROM, and the RAM has been described as an example. However, the present invention is not limited thereto. For example, the sensor device 10 may include a microprocessor having these three functions instead of the CPU, the ROM, and the RAM.

In the above-described embodiment, a case where the sensor device 10 is connected to the orthodontic appliance 700 by the fixing unit 11 has been described as an example. However, the present invention is not limited thereto.

Figure 7:
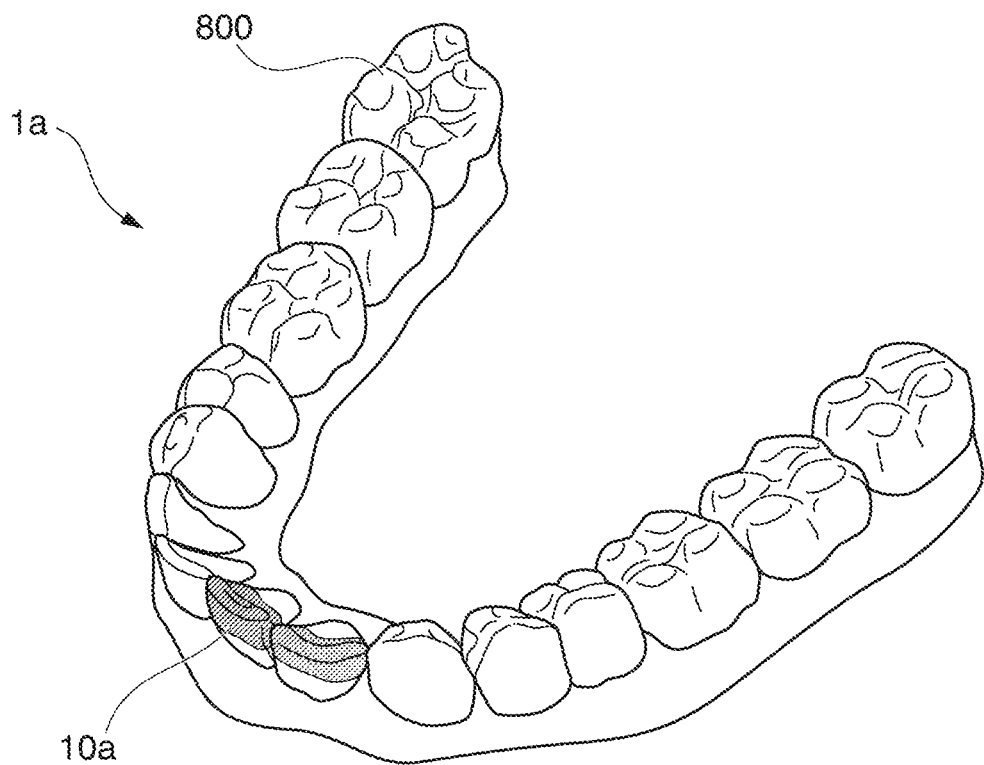
FIG. 7 is a view showing an example of an appearance of a biological monitoring device according to another embodiment.

FIG. 7 is a view showing an example of an appearance of a biological monitoring device according to another embodiment.

As shown in FIG. 7, a biological monitoring device 1*a* includes a sensor device 10*a* in a portion which covers an anterior tooth of the patient in an orthodontic appliance 800 mounted on a lower jaw of the patient. The sensor device 10*a* includes a pressure sensor that measures a fitting force of the patient.

Figure 8:
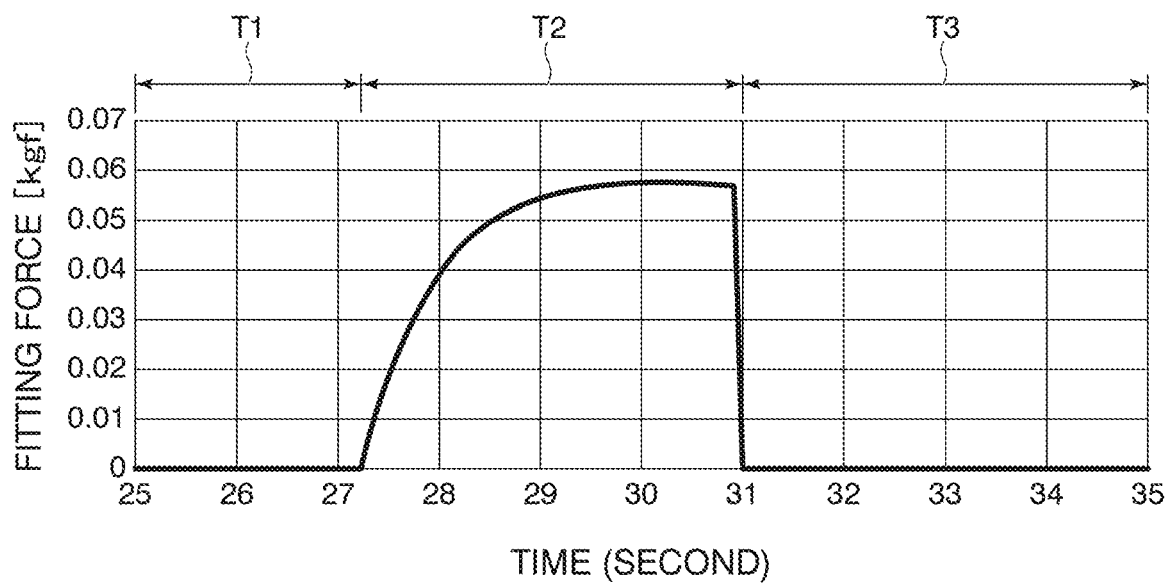
FIG. 8 is a view showing an example of a fitting force measured by a sensor device included in a biological monitoring device according to another embodiment.

FIG. 8 is a view showing an example of a fitting force measured by the sensor device included in the biological monitoring device according to another embodiment.

In FIG. 8, a horizontal axis represents a time, and a vertical axis represents the fitting force. During a period T1 and a period T3 which are shown in FIG. 8, the pressure sensor does not measure a significant magnitude of the fitting force. On the other hand, during a period T2 shown in FIG. 8, the pressure sensor measures the fitting force when the patient fits an upper jaw and a lower jaw. In a first half of the period T2, the fitting force increases as the patient starts to fit the upper jaw and the lower jaw. In a second half of the period T2, the fitting force shows a substantially constant magnitude since the patient finishes fitting the upper jaw and the lower jaw.

In this case, for example, the determination unit 132 determines that the sensor device 10 exists in the body of the patient, when the number of times that at least one of the fitting force indicated by the first detection data and the fitting force indicated by the second detection data exceeds a predetermined fitting force exceeds a predetermined number of times during a predetermined period. On the other hand, the determination unit 132 determines that the sensor device 10 does not exist in the body of the patient, when a period during which at least one of the fitting force indicated by the first detection data and the fitting force indicated by the second detection data is smaller than the predetermined fitting force continuously exceeds the predetermined period.

Hitherto, the embodiments of the present invention have been described in detail with reference to the drawings. However, specific configurations of the embodiments of the present invention are not limited to the above-described embodiments, and at least one of various combinations, modifications, substitutions, and design changes may be added to the above-described embodiments within the scope not departing from the concept of the present invention. Accordingly, the invention is not to be considered as being limited by the foregoing description and is only limited by the scope of the appended claims.

What is claimed is:

1. A biological monitoring device comprising:
   a sensor included in a sensor device, performing a detection process of detecting a medical condition of a patient, and performing a process of generating first detection data indicating a result of the detection process;
   a generation unit realized by the sensor device, and performing a process of generating second detection data indicating contents related to the detection process and having a smaller data volume than the first detection data, on a basis of the first detection data; and
   a communication unit realized by the sensor device, and performing a process of transmitting the second detection data to a terminal associated with the patient, wherein:
      when the sensor device exists in a body of the patient, the communication unit is configured to transmit the second detection data to the terminal in a first cycle, and
      when the sensor device does not exist in the body of the patient, the communication unit is configured to transmit the second detection data to the terminal in a second cycle shorter than the first cycle.

2. The biological monitoring device according to claim 1, wherein the communication unit is configured to transmit the second detection data to the terminal without receiving a request for transmitting the second detection data to the terminal.

3. The biological monitoring device according to claim 2, further comprising:
   a determination unit realized by the sensor device, and determining whether or not the sensor device exists in the body of the patient, on a basis of at least one of the first detection data and the second detection data; and
   a control unit realized by the sensor device, and controlling the communication unit to transmit the second detection data to the terminal in the first cycle, when it is determined that the sensor device exists in the body of the patient.

4. The biological monitoring device according to claim 2, further comprising:
   a determination unit calculating a time during which the sensor device does not exist in the body of the patient, on a basis of at least one of the first detection data and the second detection data, and determining whether or not the time exceeds a predetermined threshold,
   wherein when it is determined that the time is equal to or smaller than the predetermined threshold, the generation unit generates recommendation data for causing the terminal to perform a process of outputting information recommending the patient to be in a state where the sensor device exists in the body of the patient, and
   the communication unit is configured to transmit the recommendation data to the terminal.

5. The biological monitoring device according to claim 1, further comprising:
   a determination unit realized by the sensor device, and determining whether or not the sensor device exists in the body of the patient, on a basis of at least one of the first detection data and the second detection data; and
   a control unit realized by the sensor device, and controlling the communication unit to transmit the second detection data to the terminal in the first cycle, when it is determined that the sensor device exists in the body of the patient.

6. The biological monitoring device according to claim 1, further comprising:
   a determination unit calculating a time during which the sensor device does not exist in the body of the patient, on a basis of at least one of the first detection data and the second detection data, and determining whether or not the time exceeds a predetermined threshold,
   wherein when it is determined that the time is equal to or smaller than the predetermined threshold, the generation unit generates recommendation data for causing the terminal to perform a process of outputting information recommending the patient to be in a state where the sensor device exists in the body of the patient, and
   the communication unit is configured to transmit the recommendation data to the terminal.

7. The biological monitoring device according to claim 1, further comprising:
   a storage unit that is configured to store the first detection data.

8. A biological monitoring device comprising:
   a sensor included in a sensor device, performing a detection process of detecting a medical condition of a patient, and performing a process of generating first detection data indicating a result of the detection process;
   a generation unit realized by the sensor device, and performing a process of generating second detection data indicating contents related to the detection process and having a smaller data volume than the first detection data, on a basis of the first detection data;
   a communication unit realized by the sensor device, and performing a process of transmitting the second detection data to a terminal associated with the patient;
   a determination unit realized by the sensor device, and determining whether or not the sensor device exists in a body of the patient, on a basis of at least one of the first detection data and the second detection data; and a control unit realized by the sensor device, and controlling the communication unit to transmit the second detection data to the terminal in a first cycle, when it is determined that the sensor device exists in the body of the patient, wherein when it is determined that the sensor device does not exist in the body of the patient, the control unit is configured to control the communication unit to transmit the second detection data to the terminal in a second cycle shorter than the first cycle.

9. The biological monitoring device according to claim 8, wherein the determination unit is configured to calculate a time during which the sensor device does not exist in the body of the patient, on a basis of at least one of the first detection data and the second detection data, and is further configured to determine whether or not the time exceeds a predetermined threshold, and the control unit is configured to lengthen the second cycle when it is determined that the time exceeds the predetermined threshold.

10. A biological monitoring device comprising:

a sensor included in a sensor device, performing a detection process of detecting a medical condition of a patient, and performing a process of generating first detection data indicating a result of the detection process;

a generation unit realized by the sensor device, and performing a process of generating second detection data indicating contents related to the detection process and having a smaller data volume than the first detection data, on a basis of the first detection data;

a communication unit realized by the sensor device, and performing a process of transmitting the second detection data to a terminal associated with the patient, wherein the communication unit is configured to transmit the second detection data to the terminal without receiving a request for transmitting the second detection data to the terminal;

a determination unit realized by the sensor device, and determining whether or not the sensor device exists in a body of the patient, on a basis of at least one of the first detection data and the second detection data; and a control unit realized by the sensor device, and controlling the communication unit to transmit the second detection data to the terminal in a first cycle, when it is determined that the sensor device exists in the body of the patient, wherein when it is determined that the sensor device does not exist in the body of the patient, the control unit is configured to control the communication unit to transmit the second detection data to the terminal in a second cycle shorter than the first cycle.

11. The biological monitoring device according to claim 10, wherein the determination unit is configured to calculate a time during which the sensor device does not exist in the body of the patient, on a basis of at least one of the first detection data and the second detection data, and is further configured to determine whether or not the time exceeds a predetermined threshold, and the control unit is configured to lengthen the second cycle when it is determined that the time exceeds the predetermined threshold.

\* \* \* \* \*

UNITED STATES PATENT AND TRADEMARK OFFICE
CERTIFICATE OF CORRECTION

| | |
|---|---|
| PATENT NO. | : 11,800,259 B2 |
| APPLICATION NO. | : 17/474635 |
| DATED | : October 24, 2023 |
| INVENTOR(S) | : Yoshifumi Yoshida et al. |

It is certified that error appears in the above-identified patent and that said Letters Patent is hereby corrected as shown below:

On the Title Page

In Item (73) Assignees, delete second assignee "Seiko Science Energy Co., Ltd." and insert in its place -- Science Energy Co., Ltd. --.

Signed and Sealed this
First Day of October, 2024

Katherine Kelly Vidal
*Director of the United States Patent and Trademark Office*